(12) United States Patent
Mullick et al.

(10) Patent No.: US 7,894,882 B2
(45) Date of Patent: Feb. 22, 2011

(54) MINIATURE INGESTIBLE CAPSULE

(76) Inventors: Tarun Mullick, 26200 George Zeiger Dr., Suite 411, Beachwood, OH (US) 44122; Ramgopal Nair, 4520 Hemlock Cone Way, Ellicott City, MD (US) 21042; Sudhir K. Dutta, 1601 Barthel Rd., Lutherville, MD (US) 21093; Padmanabhan P. Nair, 4520 Hemlock Cone Way, Ellicott City, MD (US) 21042

( * ) Notice: Subject to any disclaimer, the term of this patent is extended or adjusted under 35 U.S.C. 154(b) by 1178 days.

(21) Appl. No.: 11/414,925

(22) Filed: May 1, 2006

(65) Prior Publication Data

US 2006/0195015 A1    Aug. 31, 2006

Related U.S. Application Data

(62) Division of application No. 09/759,398, filed on Jan. 12, 2001, now Pat. No. 7,039,453.

(60) Provisional application No. 60/180,960, filed on Feb. 8, 2000.

(51) Int. Cl.
*A61B 8/00* (2006.01)

(52) U.S. Cl. .......................... 600/476; 600/407; 600/411; 600/414; 600/104; 600/105; 600/106; 600/107; 600/109; 348/68; 348/69; 606/205; 606/206

(58) Field of Classification Search ................. 600/104, 600/105, 106, 107, 109, 407, 411, 414, 476; 606/130, 205, 206
See application file for complete search history.

(56) References Cited

U.S. PATENT DOCUMENTS

| | | | |
|---|---|---|---|
| 4,844,076 A | 7/1989 | Lesho et al. | |
| 5,279,607 A | 1/1994 | Schentag et al. | |
| 5,415,181 A | 5/1995 | Hogrefe et al. | |
| 5,481,262 A | 1/1996 | Urbas et al. | |
| 5,604,531 A | 2/1997 | Iddan et al. | |
| 5,827,190 A | 10/1998 | Palcic et al. | |

(Continued)

FOREIGN PATENT DOCUMENTS

JP    40-1076822 A    3/1989

OTHER PUBLICATIONS

"A Candid Camera for the Gut," *IEEE Spectrum*, Jul. 2000.

*Primary Examiner*—Brian Casler
*Assistant Examiner*—Baisakhi Roy
(74) *Attorney, Agent, or Firm*—Fay Sharpe LLP

(57) ABSTRACT

A miniature ingestible capsule has multiple therapeutic or diagnostic operations that can be performed. These functions are controlled by a combination of an outside control, a pose beacon and through information relayed from an imagining array and transmitter. These functions can be in a separate capsule without an imaging array or within the same capsule with an imaging array. Typically, there is one function performed in addition to imaging. These functions can include suction and spray capabilities, ultrasound sensor, lithotripsy, laser, heat, electrocautery, BICAP, biopsy forceps, a needle knife snare cautery (cold and hot with continuous or pulsed current for cutting and coagulation), with a basket, and fine needle aspiration with various wheels and fins and motors controlled externally and other tools to be used in humans. All of these tools can be attached to a retractable arm. Also, they can be used on an elevator device that lifts them, allowing for an extra 180° of movement.

24 Claims, 8 Drawing Sheets

U.S. PATENT DOCUMENTS 5,842,977 A    12/1998  Lesho et al.
5,993,378 A *  11/1999  Lemelson .................. 600/109
6,187,026 B1 * 2/2001   Devlin et al. ................ 606/205
7,515,953 B2 * 4/2009   Madar et al. ................ 600/476

* cited by examiner

MINIATURE INGESTIBLE CAPSULE

This application is a divisional of U.S. patent application Ser. No. 09/759,398, filed Jan. 12, 2001 now U.S. Pat. No. 7,039,453, and U.S. provisional application Ser. No. 60/180,960, filed Feb. 8, 2000, the disclosure of which is incorporated herein by reference.

FIELD OF THE INVENTION

This invention relates to a miniature ingestible capsule for imaging the gastrointestinal tract for medical diagnosis or diagnosis and/or therapy for the human body. More specifically, this invention relates to noninvasive, noninterventional methods for internal examination of the gastrointestinal tract or other internal therapy and diagnosis of the human body that are significantly more convenient, comfortable, lower in cost and more advanced compared with current invasive diagnostic methods such as colonoscopy, sigmoidoscopy, esophagogastroduodenoscopy and push enteroscopy.

BACKGROUND OF THE INVENTION

The mammalian gastrointestinal tract comprises the esophagus, stomach, small intestine, and colon. Physicians image the interior of the gastrointestinal tract to aid in the diagnosis and treatment of many illnesses such as ulcers, growths, cancers and bleeding spots. More specifically, these conditions include colorectal cancer, colonic polyposis, inflammatory bowel disease, irritable bowel syndrome, Barrett's esophagus, peptic ulcer disease and dyspepsia.

Colorectal cancer, for example, is the second leading cause of cancer death in the United States, with 133,500 new cases detected in 1996, 54,900 (41%) of which resulted in death. (Agency for Health Care Policy & Research (AHCPR) Research Activities 200:15-16, 1997.) Survival rates improve and treatment costs decline with early detection of the process. (Brown, M. L. and Fintov, L. The economic burden of cancer. In Greenwald, P. Kramer, B. S., and Weed, D. L., eds Cancer Prevention and Control. New York, Marcel Decker, pp. 69-81, 1995. Healthy People 2000: Nutritional Health Promotion and Disease Prevention Objectives. U.S. Department of Health and Human Services, Public Health Service, DHHS Publication No. (PHS) 91-50212, p. 423, 1991.) However, regular screening for colorectal cancer is not performed for the vast majority of the populace due to the high cost of such programs and, more importantly, the reluctance of a healthy population at risk to undergo an invasive procedure again and again for surveillance against cancer. As a result, over two-thirds of patients are diagnosed with advanced disease. (Eddy, D. M. Screening of colorectal cancer Ann. Int. Med. 113:373, 1990).

The only low-cost noninvasive screening tests for colorectal cancer are fecal occult blood tests, which look for the presence of fecal occult blood in stool specimens. These tests exhibit poor sensitivity due to the fact that malignant growths of the colon have to be fairly large before they start to bleed. Furthermore, there are many other reasons for bleeding into the gastrointestinal tract (e.g., ulcers) which lead to low specificity of the test and a high probability of false positives. (Eisner, M. S., and Lewis, J. A. Diagnostic yield of positive FOBT found on digital rectal examination. Arch. Int. Med. 151:3180, 1991. Rockey, D. C., Koch, J., Cello, J. P., Sanders, L. L., McQuaid, K. Relative Frequency of Upper Gastrointestinal and Colonic Lesions in Patients with Positive Fecal Occult-Blood Tests.) Even with the poor characteristics of fecal occult blood tests, the American Cancer Society estimated that the regular use of the test in men over age 50 could produce a 15% reduction in mortality. (Agency for Health Care Policy & Research (AHCPR) Research Activities 200: 15-16, 1997.)

The most common diagnostic procedure for colonic examination is colonoscopy. This procedure involves the optical examination of the entire colon using a device known as a colonoscope. A colonoscope comprises a flexible tube containing a fiber optic imaging and illuminating device and a device to resect portions of the surface of the intestinal tract. The colonoscope is inserted into the rectum and can be maneuvered to the ileo-cecal junction (the start of the colon). The operator views the image on a video display. The medical team performing this procedure usually comprises a gastroenterologist, specially trained nurses and at times an anesthesiologist. Polyps (tumors) are identified visually and biopsied. If examination of the specimen reveals malignancy, a surgical team resects the regions containing the tumors. Usually, this is followed by a period of chemotherapy, administered to fight unobserved or secondary tumors; annual colonoscopies may be prescribed. Considering the cost of the colonoscopy alone, a yearly colonoscopy for all patients over age 48 for instance, would be prohibitively expensive. Colonoscopy for asymptomatic patients is seldom prescribed.

The sigmoidoscope is similar to a colonoscope, but can only be used to image the lower ⅔ of the colon. Although simpler than a colonoscope, its operation still requires the presence of a highly trained physician and often requires sedation.

The esophagogastroduodenoscope is used to image the upper gastrointestinal tract, namely, the esophagus, the stomach and the duodenum. It is inserted through the mouth. Again, its operation requires the presence of a highly trained physician and often requires sedation.

The esophagogastroduodenoscope is used to identify ulcers, gastritis, AVMs, esophagitis, varices, duodenitis, Barrett's esophagus, hiatal hernias and tumors. The esophagogastroduodenoscope procedure is performed on patients with a variety of symptoms that include nausea, vomiting, abdominal bloating, abdominal pain, heartburn, reflux, family history of cancer, jaundice, weight loss, anemia, and gastrointestinal bleeding. A majority of those procedures are diagnostic. Considering the cost of endoscopy and the sedation requirement, it would be prohibitively expensive to perform esophagogastroduodenoscopy on all patients with symptoms.

The push enteroscope is used to image the third and fourth portions of the duodenum and the proximal jejunum. It is inserted through the mouth. Its operation requires the presence of a highly trained physician and requires sedation. The push enteroscope may be used to detect arteriovenous malformations and small intestinal tumors.

The endoscopic retrograde cholangiopancreatograph procedure is done to visualize, to treat, and to diagnose pancreatic and biliary diseases. The endoscopic ultrasound and transesophageal ultrasound are used to image the esophagus, adjacent mediastinal structures, lungs, pancreas, aorta and other vessels, colon and heart. These techniques allow for tissue aspiration through a fine needle. Each of these procedures involve the passage of and endoscope through the mouth. Their operation requires the presence of a highly trained physician and a lot of sedation.

The present invention is a type of non-tethered device that is ingested by the patient, thereby passing through the entire gastrointestinal tract, sending images and data through a telemetry means. There are several prior systems that use an ingestible device to provide data on the internal state of a patient. The Heidelberg capsule relays pH information through a radio frequency (RF) link, and can release medicament on a signal from an external transmitter. The Konigsberg capsule monitors temperature and uses a RF link. The Cortemp pill, which is commercially available at this time, also monitors the body temperature, but uses a near-field magnetic link.

More sophisticated approaches such as colonoscopy and related gastrointestinal imaging methods, namely, sigmoidoscopy and esophagogastroduodenoscopy, are more effective because they can identify abnormalities before the occurrence of late-stage symptoms (e.g., blood in the stools for colonic tumors or tarry stools for peptic ulcers) However, these methods see limited use for several reasons. One, they are invasive and uncomfortable to the patient, requiring sedation so that a flexible fiberoptic tube can be inserted into the tract. This is a major limitation of these tests in their application to healthy asymptomatic individuals for repeated examinations (every 1-3 years).

Secondly, these tests are expensive, requiring the presence of a physician and other personnel. Third, they are inconvenient, requiring the patient to take a purgative, fast overnight, and remain incapacitated during the procedure.

Thus, there is a medical and economic benefit for an inexpensive, noninvasive, miniature, ingestible imaging or diagnostic device that allows the patient to use the device while still performing the normal activities of daily living. Furthermore, it would eliminate the need for highly trained personnel for its operation. In light of the high cost of current imaging methods (and their subsequent limited and late-stage application), hospitals, clinical laboratories, and Health Management Organizations (HMOs), will be able to employ these devices as a cost-containment strategy.

Accordingly, it has been considered desirable to develop a new and improved miniature diagnostic and therapy device which would overcome the foregoing difficulties and others and meet the above-stated needs while providing better and more advantageous overall results.

BRIEF SUMMARY OF THE INVENTION

The present invention relates to a miniature capsule. More particularly, it relates to a miniature non-digestible capsule, ingestible by a human or other animal for performing internal diagnostic or therapeutic functions.

One embodiment of the capsule comprises an impermeable anterior and posterior membrane, a transparent window, an imaging device, a pose beacon, a transmitter, and a power supply, and an external unit comprising a data reception device, a recording device, and a pose detection system. Ingested by a patient, the capsule will pass through the entire gastrointestinal tract of the patient, providing real-time circumferential images of the esophagus, stomach, small intestine, and colon, which can be viewed and recorded by the physician. The capsule exits the patient through the rectum. The device can either be discarded or reused by replacing the membranes.

A miniature color imaging device, such as a CCD array and lens, and an illumination device, such as an RGB diode array or similar low-power white light source provide real-time color images of the gastrointestinal tract. The image is transmitted in real-time by a transmitter, such as a miniaturized UHF video transmitter, to an external reception device, such as a television monitor and a recording device, such as a video cassette recorder. The capsule may be weighted in such a way as to maintain a particular orientation in the stomach. In simultaneous operation with the imaging system is a six degree-of-freedom pose detection device that calculates the real-time pose of the capsule, thus tracking the device through patient's body relative to a fixed external reference frame that may be strapped to the patient's abdomen.

In one arrangement, this device is a passive beacon which is tracked by an external detector strapped to the patient's body, which relays pose data that is correlated with received video data by a computer. Alternatively, the pose detector may be an active device whose data is either multiplexed with the image data prior to transmission or is sent on a second channel of the telemetry device. An electric power source such as a lithium battery provides sufficient energy to power all the component devices for a time period of at least 72 hours, the maximum transit time for the gastrointestinal tract. (The average transit time is 48 hours, with a range of 24 to 72 hours.)

The pose detector is not absolutely necessary for the successful use of this device. A trained physician will likely be able to infer the approximate location of a given image from its appearance and the time it is recorded (since the range of transit times through the parts of the tract are well documented).

In another form, the capsule includes a reception capability, such as a radio-frequency receiver, and an internal microprocessor that allows instructions to be relayed from the physician to the capsule. Miniature motors allow the imaging system to be reoriented, or provide some form of "controlled mobility," which could include a remote control, joystick, mouse control or other computer-directed or voice-directed control or other control. An expandable bladder attached to the capsule can be expanded to stabilize the capsule or slow its motion through the tract. The system may also include on-board signal processing circuitry to automatically stabilize the image. Alternatively, a micro-machined mechanical stabilization platform can be built into the imaging system. The imaging system may also include a means such as a prism or fiber-optic device, to direct multiple images onto the imaging device.

In an alternate embodiment, a capsule would comprise an anterior membrane with a port for an ultrasound sensor, a transmitter, a pose beacon, a power source, and a posterior membrane. The capsule would not include an imaging device or lens.

The anterior membrane is made of a non-allergenic, non-digestible, impervious material. The port is curved to match the curvature of an outside surface of the anterior membrane. The posterior membrane is also made of a non-allergenic nondigestible impervious material, and may include an integrated antenna for the transmitter.

Other forms of the capsule have the capacity for specialized tools including biopsy forceps and snares (with cold and hot snares with coagulation and cutting current) for purposes like polypectomy and baskets for retrieval and rat tooth forceps for retrieval and for other miniature specialized devices. The operation of these devices is controlled in a similar fashion to the position of the capsule. Local mucosal resection can be performed in one embodiment with a combination of hot snare cautery and suction. Furthermore, another form has treatment tools using, for example, heat and electro cautery current, BICAP current, argon plasma coagulation and laser current. All these currents can be continuous or time pulsed in cutting or coagulation modes. Each of these embodiments mentioned above can be designed with the imaging apparatus or without the imaging apparatus.

These tools can be connected to an elevator device within the capsule allowing an extra range of movement of 180° for the tools.

One aspect of the present invention is the provision of a method for imaging a gastrointestinal tract that uses an ingestible device that allows a patient to use the device while still performing normal activities of daily living.

Another aspect of the present invention is that it would eliminate the need for highly trained personnel for its operation.

Yet another aspect of the present invention is that it is economically affordable and less expensive than existing methods of imaging gastrointestinal tracts.

Still another aspect of the present invention is that it is easier to implement and allows patients to be examined more frequently than existing methods of imaging gastrointestinal tracks.

Still other functions and benefits of an embodiment of the invention include the ability to provide ultrasound imaging with a miniature ultrasound sensor and to image and treat problems with the pancreatic and biliary ducts and gastrointestinal system and the rest of the human body. In another embodiment, with a special dye injection port for various dyes imaging of, for example, the biliary and pancreatic ducts and the rest of the human body can be done. Treatment apparatus ports allow for cutting and coagulation currents to be delivered locally.

Furthermore, a focal laser treatment, argon plasma coagulator treatment, lithotripsy treatment with ultrasound current can be used in the biliary and pancreatic ducts, gastrointestinal system and rest of human body in other forms of the invention. In addition, tools including miniature baskets, miniature snares, miniature needles with epinephrine (for example) and other treatments, miniature forceps, miniature cytology brushes can be included in a form of the capsule for diagnosis and treatment in the biliary and pancreatic trees, pancreas, liver, and gastrointestinal system, and human body. Also, a thin wire, catheter, miniature plastic or metal stint can be deployed in the biliary and pancreatic ducts in other forms of the capsule. Finally, the capsule has suction capabilities to remove unwanted debris and can sprinkle water and n-acetyl cysteine locally over the lens or capsule to remove residual debris from the gastrointestinal system to improve or enhance visualization, diagnostic, therapeutic or other functions of the capsule.

Still other benefits and advantages of the present invention will become apparent to those skilled in the art upon a reading and understanding of the following detailed specification.

BRIEF DESCRIPTION OF THE DRAWINGS

The invention may take form in certain parts and arrangements of parts, embodiments of which will be described in detail in this specification and illustrated in the accompanying drawings which form a part hereof and wherein.

DETAILED DESCRIPTION OF THE PREFERRED EMBODIMENTS

Figure 1:
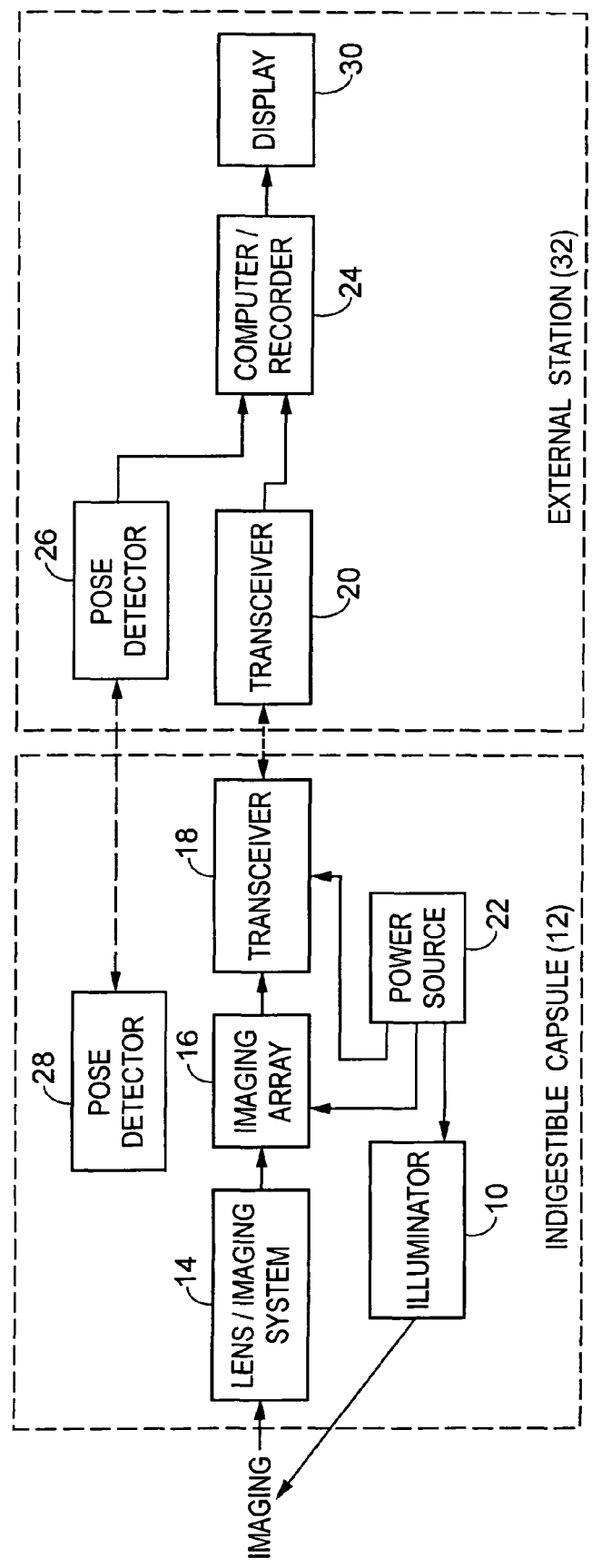
FIG. 1 is a diagram showing the main components and signal flow for the imaging system.

Referring to the drawings, wherein the showings are for purposes of illustrating preferred embodiments of this invention only, and not for purposes of limiting same, FIG. 1 shows a block diagram for the device. An illuminator 10 inside the capsule 12 projects light into the gastrointestinal tract. Images enter the capsule through a lens 14, impinging on an imaging array 16, the signal from which is then transmitted by a transceiver 18 to a transceiver 20 outside of the capsule. A power source 22 inside the capsule provides power to the imaging array 16, transceiver 18, and illuminator 10. The data from the transceiver 18 is then relayed to a recording and display device 24. Simultaneously, a pose detection system 26 tracks a beacon 28 located inside the capsule and relays tracking information to the recording and display system 24, which forms a display 30.

There are several external components to the external station 32. The basic system only requires the transceiver 20 to capture the image information. A more complex design would include a transmitter in the external station and a receiver in the capsule, enabling the external controller to transmit instructions to the capsule itself. The pose detection system 26 is a powered device that produces an RF signal or EM field that allows the capsule's beacon to be tracked. The device can be strapped to the patient's body. The pose data can be read by the recording and display device 24 and correlated with the image data. The recording and display device 24 may be used to record and integrate the image and pose data and data from other sources such as a CAT scan or MRI, and produce a display 30 for the physician.

Figure 2:
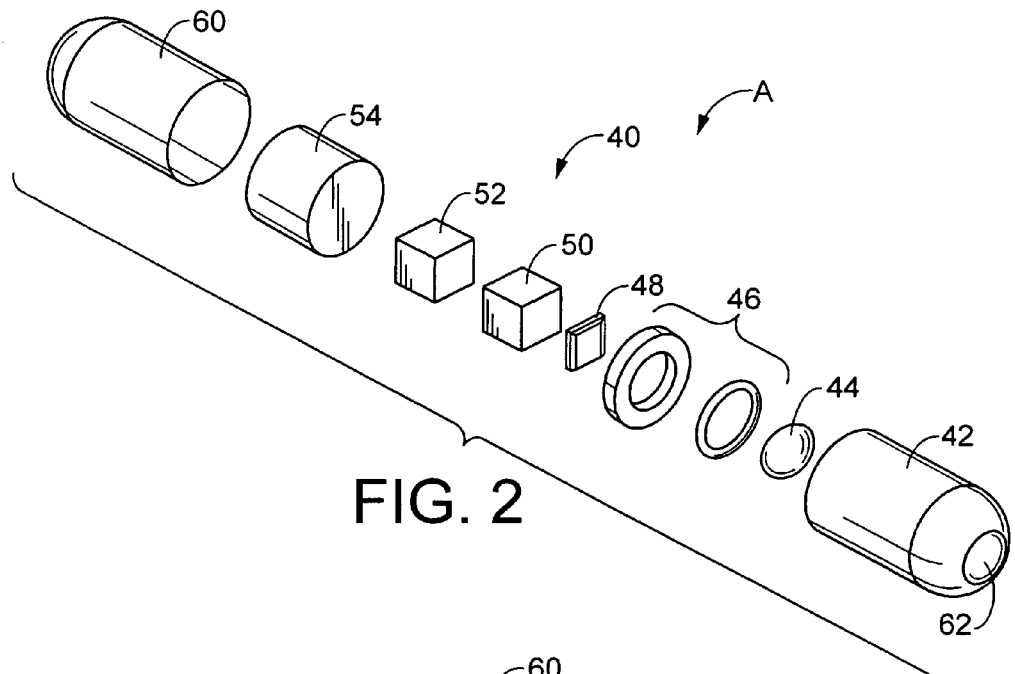
FIG. 2 is an exploded view of the capsule in accordance with the first embodiment of the present invention.

Referring to FIG. 2 in accordance with the first preferred embodiment of the present invention, an imaging device A includes a capsule 40 including an anterior membrane 42 through which images are viewed, a lens 44 positioned within the membrane, an illumination device 46 (comprising a light source and projection device) positioned adjacent to the lens, an imaging array 48, transmitter 50, a pose beacon 52, a power source 54, and a posterior membrane 60.

The anterior capsule membrane 42 is made of a non-allergenic, nondigestible, impervious material with at least one transparent window or opening 62 for the lens 44. The window 62 is curved to match the curvature of an outside surface of the anterior membrane 42. The posterior membrane 60 is also made of a non-allergenic nondigestible impervious material, and may include an integrated antenna (not shown) for the transmitter.

Figure 3A:
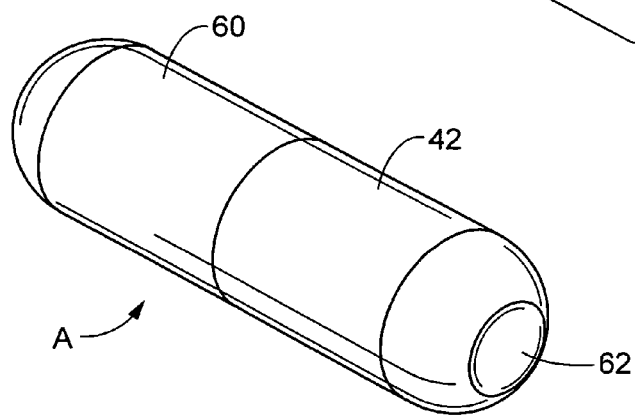
FIG. 3A is a perspective view of the capsule with an internal lens and a transparent window in the membrane in accordance with the first embodiment of the present invention.
Figure 3B:
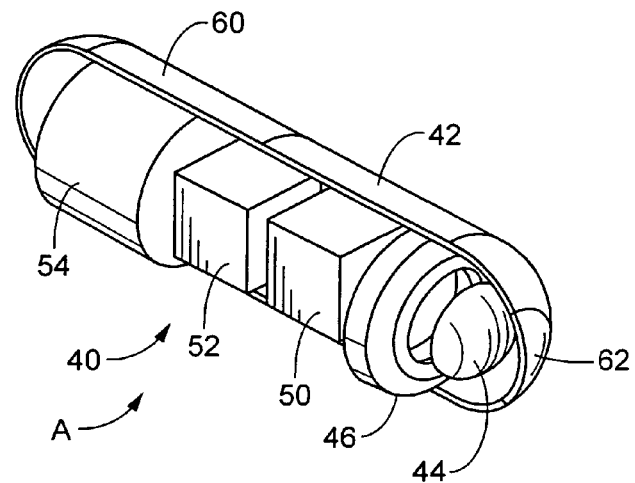
FIG. 3B is a sectional view of the capsule of FIG. 3A.

FIGS. 3A and 3B show the capsule 40 in the assembled configuration. The transparent window 62 is made of a material to which mucous and other biological materials will not adhere. An additional advantage of an internal lens design is that the lens can be mounted at an optimal distance to maintain focus.

The lens 44 may be mounted behind the transparent window 62 in the capsule, or it may be mounted in an opening in the capsule so that its front surface is exposed to the outside. The lens 44 may be a plastic or glass lens, a prism or a fiber optic bundle. One advantage of a fiber optic bundle is that its front end can be designed to image several views of the external environment, thus producing a composite image on the array plane. The focal length of the imaging system must be small enough to achieve infinite focus at approximately 1 mm.

The simplest and most cost effective imaging array 48 is a CCD (charge-coupled device) array. It may be necessary to provide shielding for the CCD array to prevent RF interference from the transmitter. A slightly oversized CCD array plus digital signal processor (DSP) circuitry can be included to allow real-time stabilization of the image, by time-correlating a series of images from the oversized array to illuminate image blur and shake electronically. New micromachining technologies may be included in the array itself to provide image stabilization. These devices would essentially incorporate a passive or active damping system into the CCD chip itself. To maximize space for additional circuitry such as a DSP for on-board image processing, signal multiplexing and signal encoding can be constructed on flexible circuit board that can wrap circumferentially around the inside of the capsule.

The type of illuminating device or light source 46 depends to a certain extent on the choice of imaging array. The use of a low-lux imaging array obviates the need for a high-power light source. The source should approximate a white light source so that a color image can be obtained. Methods for producing a white light source at very low power include 3-diode light source, inorganic LEDs, and full-color organic electroluminescent sources. FIG. 2 shows a light source 46 which is toroidally shaped and backed by a ring-semi-parabolic mirror, concentric with the window 62 and lens 44.

The pose beacon 52 provides a useful auxiliary piece of information, the real-time position of the capsule relative to the patient's body. This information will eliminate the discomfort of a tether or the guesswork necessary in pinpointing the location of abnormality by simple visual examination of the video or by time-tracking the video. There currently exist several proven methods to determine the six degree-of-freedom pose of a remote object, most often used in robotics to track mobile robots or to digitize human movements, for example, in hand-tracking and head-tracking controllers. These devices use a RF or EM beacon that reflects signals from an externally fixed transmitter, somewhat like a miniature radar system. Distances are typically limited to a few meters cubic, which fall well within the specifications for this device. The beacons are passive devices and will not draw power from the onboard battery. External stations that can be strapped or belted to the patient provide the signal sources. Given the recorded time-spacing tracking information, there are numerous ways to develop a correspondence between the video images and the patient's internal structures. For example, a computer can overlay the time-parametrized space-path of the capsule on an image based on CAT scan or MRI of the patient, or over a computer-generated model based on the patient's body size and shape. The video can then be synchronized with the capsule's motion on the computer screen.

The capsule requires a transmitter 50 rather than a transceiver. The simplest approach is to use a miniature amplitude modulation (AM) video transmitter in the 400 MHz-1.5 GHz region. Other standard transmission methods include frequency modulation (FM), pulse-code modulation (PCM), and frequency shift keying (FSK). For more complex arrangements, an on-board receiver will allow the base station to communicate with the capsule.

The power source 54, is a device of relatively high energy density, capable of 10's of mA in the 0.5-9V range (these numbers are for the current commercially available CCD and RF devices). The power source 54 must fit within approximately ½ the volume of the capsule, approximately ⅓ cc, and must run the device for 72 hours at the body temperature (approximately 37° C). Additionally, the nature of the imager will determine the amount of light necessary to provide the desired image quality.

Off-the-shelf ⅓" CCD board-cameras have power requirements in the range of 50-200 mA at 9VDC. However, a portion of this requirement is for the line driver, which enables the output signal to be sent on a long coaxial cable (e.g., 60" plus). Since a line driver is not a requirement for this device, we can expect a much lower current requirement. Off-the-shelf video transmitters require approximately 50 mA current at 9V. These devices, however, transmit signals at a design distance of 100-500".

The power source or battery 54 may also be designed to act as the ballast to orient the capsule in the stomach. In other words, the battery will be situated to the posterior of the capsule.

There are several lithium battery types currently used in implantable biomedical applications. One type is lithium iodine. These are currently used in implantable cardiac pacemakers; microamp range over long periods, a 4 mm thick 10 mm radius disc has an energy volume of 400 mA-hrs. Lithium Silver Vanadium Oxide batteries are used in both high amperage applications (e.g., defibrillator) and medium amperage applications (e.g., neurostimulators) and have a current of 50 mA continuous. Lithium Carbon Monofluoride batteries are used in medium amperage applications such as neurostimulators and drug infusion pumps.

The battery 54 will include some form of integrated on-off switch for the capsule, activated, for example, by twisting the posterior capsule with respect to the anterior capsule, or similar method that will not be accidentally actuated by peristalsis of the gut.

Figure 4A:
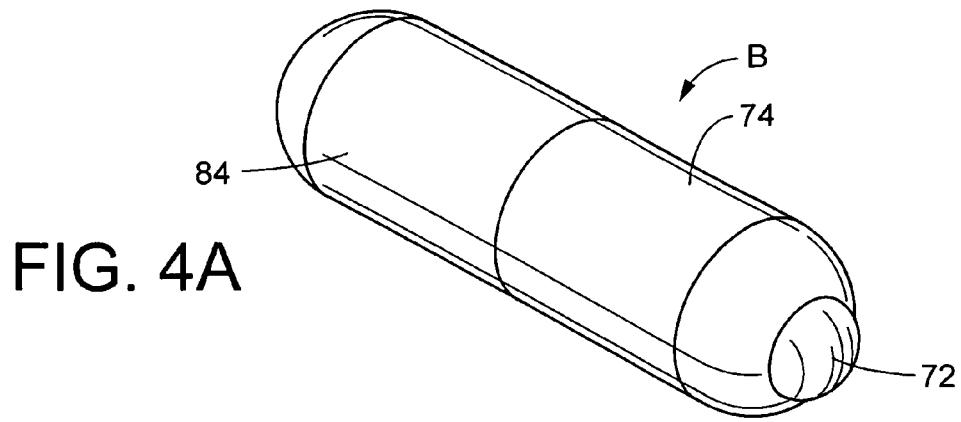
FIG. 4A is a perspective view of the capsule with an external lens in accordance with a second embodiment of the present invention.
Figure 4B:
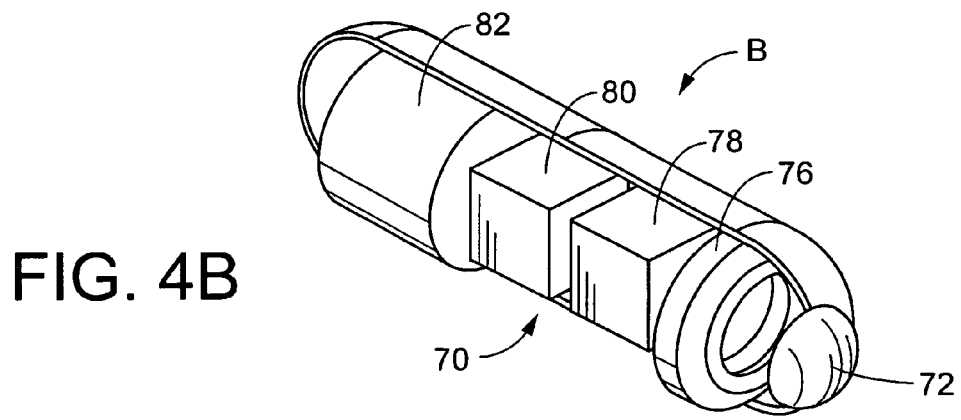
FIG. 4B is a sectional view of the capsule with an external lens of FIG. 4A.

Referring now to FIGS. 4A and 4B, an imaging device B includes a capsule 70 with an external lens 72 in accordance with a second preferred embodiment of the present invention is shown. The front surface of the lens is exposed to the external environment. The lens 72 is positioned on an outside surface of an anterior membrane 74 of the capsule. This embodiment does not have a window. As discussed above, the capsule further includes an illumination device 76, an imaging array (not shown), a transmitter 78, a pose beacon 80, a power source 82, and a posterior membrane 84. In case the desired lens material is not ideal for limiting fluid adherence, such that fluids may build up on its surface and reduce image quality, a transparent window may be used.

Figure 5A:
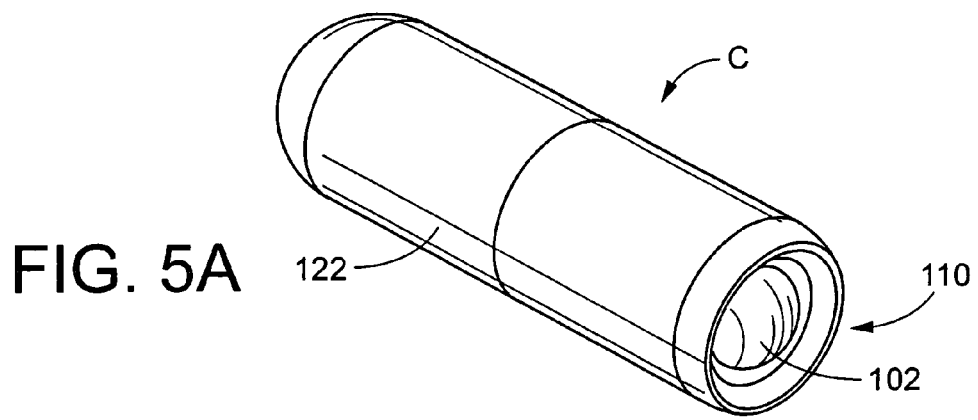
FIG. 5A is a perspective view of a capsule with an internal lens and a flat transparent window in the membrane in accordance with a third embodiment of the present invention.
Figure 5B:
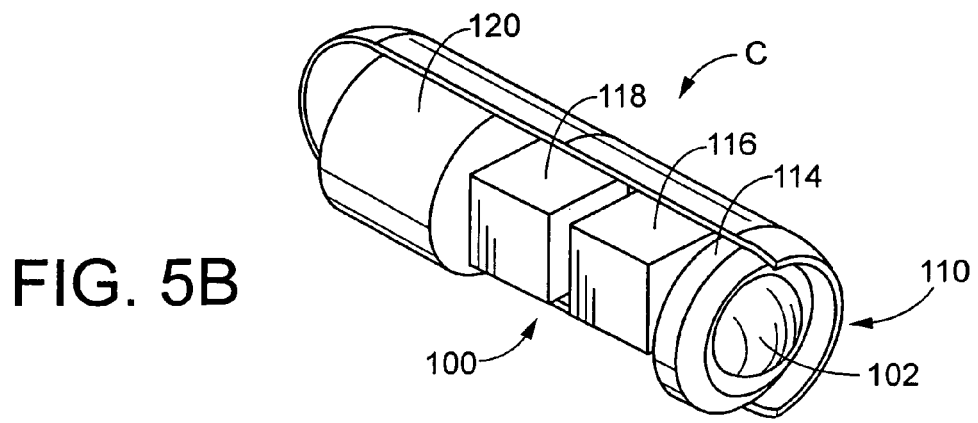
FIG. 5B is a sectional view of the capsule of FIG. 5A.

Referring now to FIGS. 5A and 5B, an imaging device C includes a capsule 100 in accordance with a third preferred embodiment of the present invention is shown. The capsule 100 has an internal lens 102 and a flat transparent window 110 in the membrane.

The capsule further includes an illumination device 114, an imaging array (not shown), a transmitter 116, a pose beacon 118, a power source 120, and a posterior membrane 122.

Figure 6:
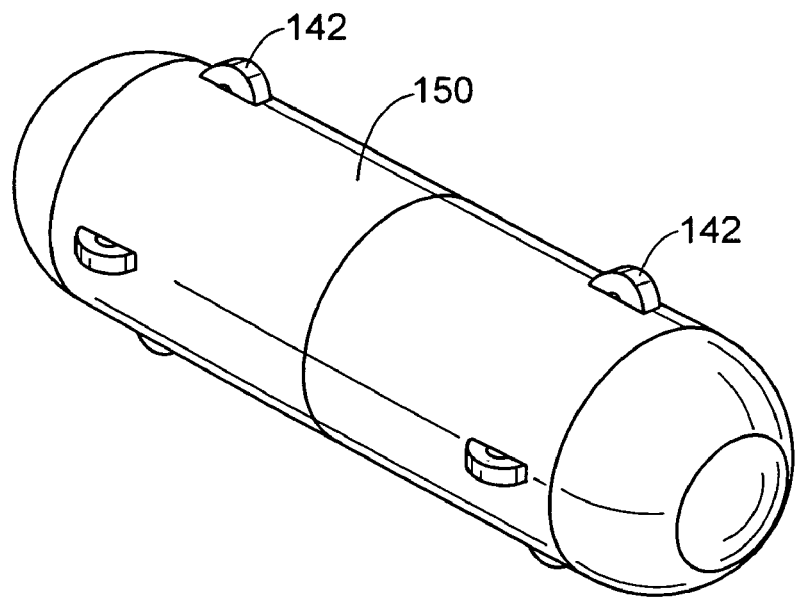
FIG. 6 is a perspective view of a capsule with wheels in accordance with a fourth embodiment of the present invention.

Referring now to FIG. 6, wheels 140 may be added to the capsule 150 in accordance with a fourth embodiment of the present invention. The capsule may be one of the three embodiments previously described. The wheels would be powered by a remote control device (not shown). The wheels 140 would have spokes 142 which would provide friction and enable the wheels to move along surfaces. The capsule with wheels would be used primarily for situations where the stomach is virtually dry, not fluid filled, such as a result of the patient fasting. Two sets of four wheels 140 equally spaced may be placed around the circumference of the capsule. Also, the capsule with wheels may be used in addition to a second capsule. The capsule with wheels may provide a therapeutic function instead of a diagnostic function. That is, the capsule may supply medicine or perform another therapeutic function to the area being investigated by the second capsule. One capsule would not be able to detect the area being investigated through a video system as well as provide medicine or other therapeutic relief.

Figure 7:
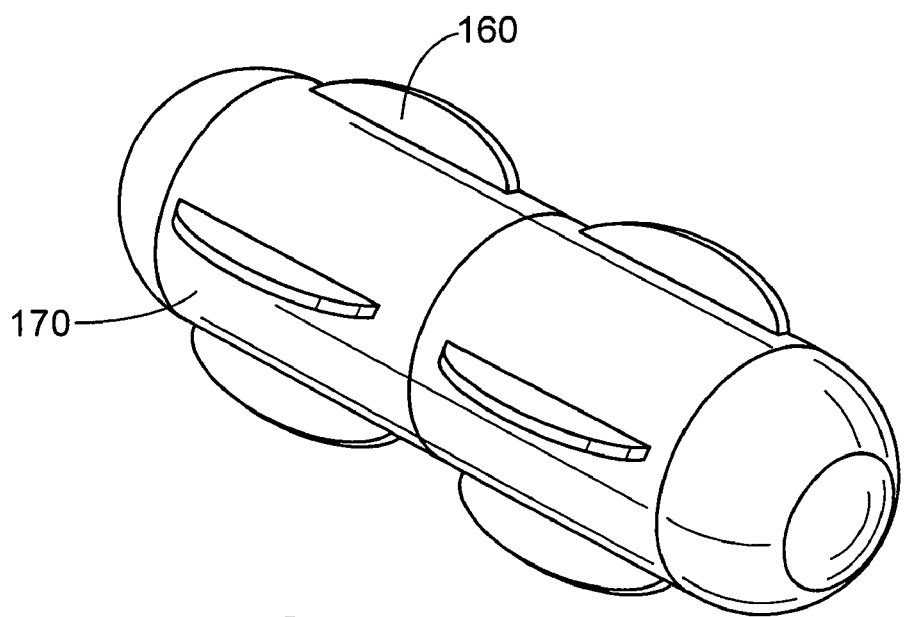
FIG. 7 is a perspective view of a capsule with fins in accordance with a fifth embodiment of the present invention.

In the situation where the stomach is at least partially fluid-filled, fins 160 in lieu of wheels may be placed on the exterior surface of capsule 170 as illustrated in a fifth embodiment in FIG. 7. The fins 160 would aid the capsule in moving throughout the stomach.

Figure 8:
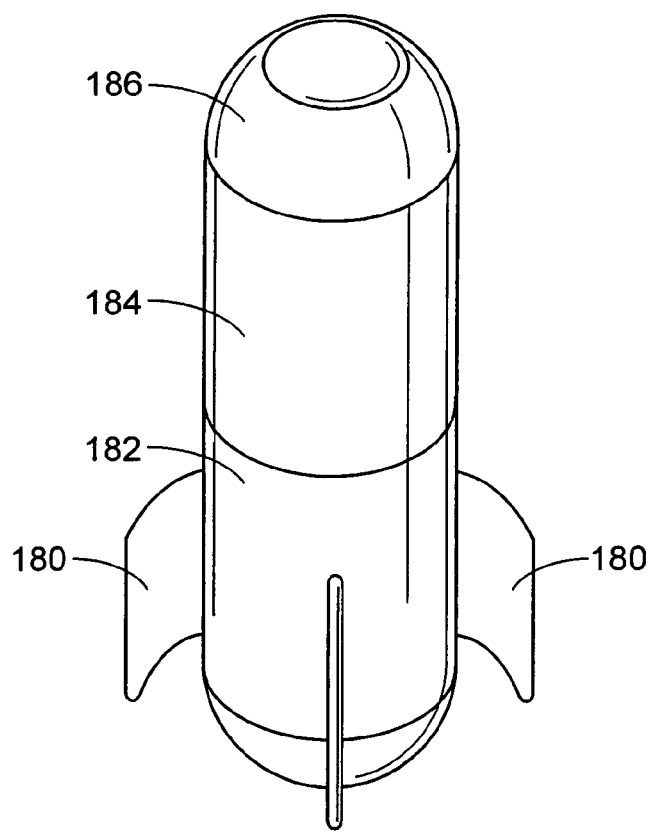
FIG. 8 is a perspective view of a capsule with prongs on a posterior membrane of the capsule in accordance with a sixth embodiment of the present invention.

In a sixth embodiment, referring to FIG. 8, prongs 180 would extend from posterior end 182 of capsule 184. The prongs 180 can be retractable and would serve as a base for the capsule to effectively anchor or stabilize the capsule. A laser or biopsy forceps (not shown) could extend from the anterior portion 186 of the capsule.

Figure 9:
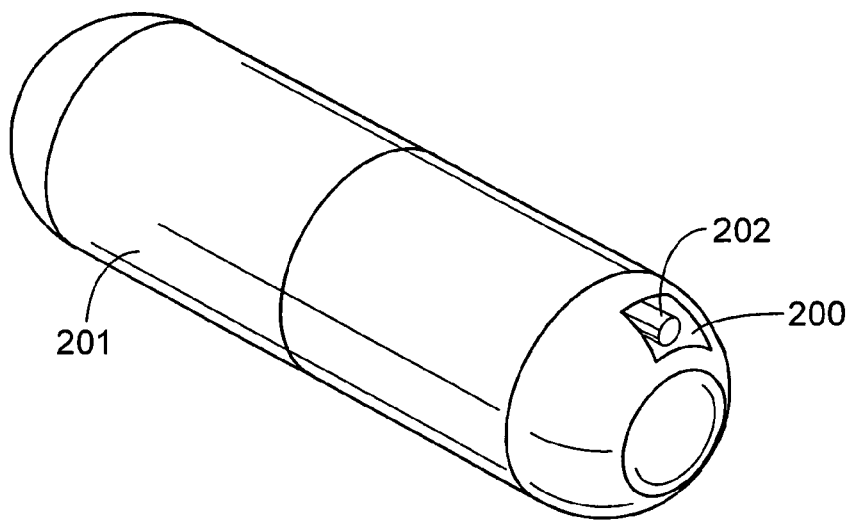
FIG. 9 is a perspective view of a capsule with a port and a treatment tool in accordance with a seventh embodiment of the present invention.

In seventh embodiment, referring to FIG. 9, a port 200 is provided in capsule 201 with an opening for a treatment tool 202, such as a laser or ultrasound, sensor. Alternatively, the treatment tool 202 can be an argon plasma coagulator, BICAP or a dye injection device or a heat cautery.

Treatment tool 202 can include heat and electro cautery current, BICAP current, argon plasm coagulation or laser current. All these currents can be continuous or time pulsed in cutting or coagulation modes.

Ultrasound scanning or ultrasonography is a technique to image human tissue. By definition, ultrasound is a sound wave having a frequency greater than 20 khz. The sound waves used in ultrasonography are produced form a device called a transducer. Arrays of ultrasonic waves scan tissue and are reflected back to the transducer.

Still other functions and benefits of an embodiment of the invention include the ability to provide ultrasound imaging with a miniature ultrasound sensor and to image and treat problems with the pancreatic and biliary ducts and gastrointestinal system and the rest of the human body. In another embodiment, with a special dye injection port for various dyes imaging of, for example, the biliary and pancreatic ducts and the rest of the human body can be done. Treatment apparatus ports allow for cutting and coagulation currents to be delivered locally.

Furthermore, treatment tool 202 can include a focal laser treatment, argon plasma coagulator treatment, or lithotripsy treatment with ultrasound current which can be used in the biliary and pancreatic ducts, gastrointestinal system and rest of human body in other forms of the invention.

Figure 10:
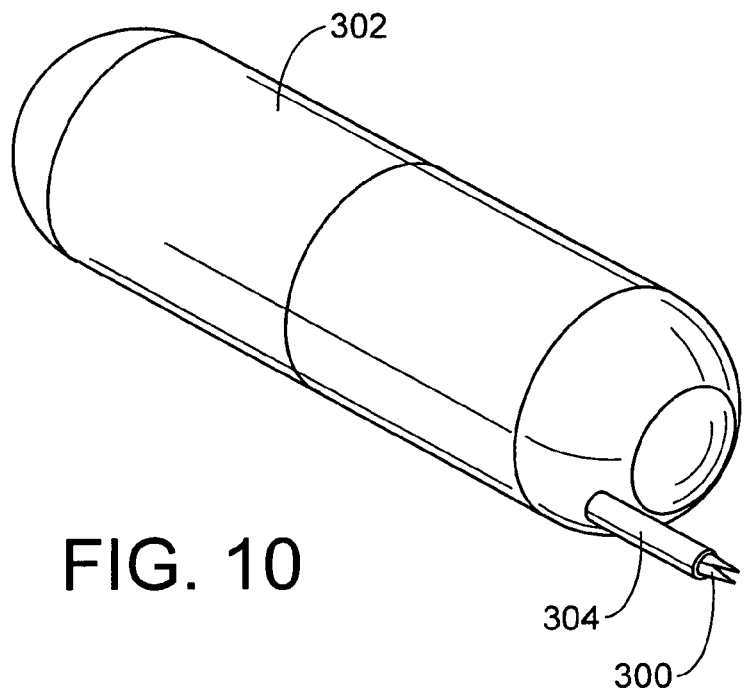
FIG. 10 is a perspective view of a capsule with a treatment tool such as extendable biopsy forceps or extendable basket, retractable basket, retractable rat tooth forceps, retractable cytelogy brush, retractable snares or other miniature devices for diagnosis and therapy in the human body in accordance with an eighth embodiment of the present invention.

In an eighth embodiment (FIG. 10), a treatment tool 300 is added to a port in the front portion of the capsule 302. A retractable lever 304 protrudes from the capsule exposing the tool 300. Upon completion of the treatment operation, the tool may be retracted within the capsule.

The specialized tool 300 can include biopsy forceps or retractable snares (with cold and hot snares with coagulation and cutting current) for purposes like polypectomy. Alternatively, tool 300 can include an extendable basket, retractable basket, retractable rat tooth forceps, retractable cytology brush, which can be used for diagnosis and therapy in the human body. Miniature snares, miniature needles with epinephrine (for example) and other treatments, miniature forceps, miniature cytology brushes can be included in a form of the capsule for diagnosis and treatment in the biliary and pancreatic trees, pancreas, liver, and gastrointestinal system, and human body. The operation of these devices is controlled in a similar fashion to the position of the capsule. Local mucosal resection can be performed in one embodiment with a combination of hot snare cautery and suction. Each of these embodiments mentioned above can be designed with the imaging apparatus or without the imaging apparatus.

Figure 11:
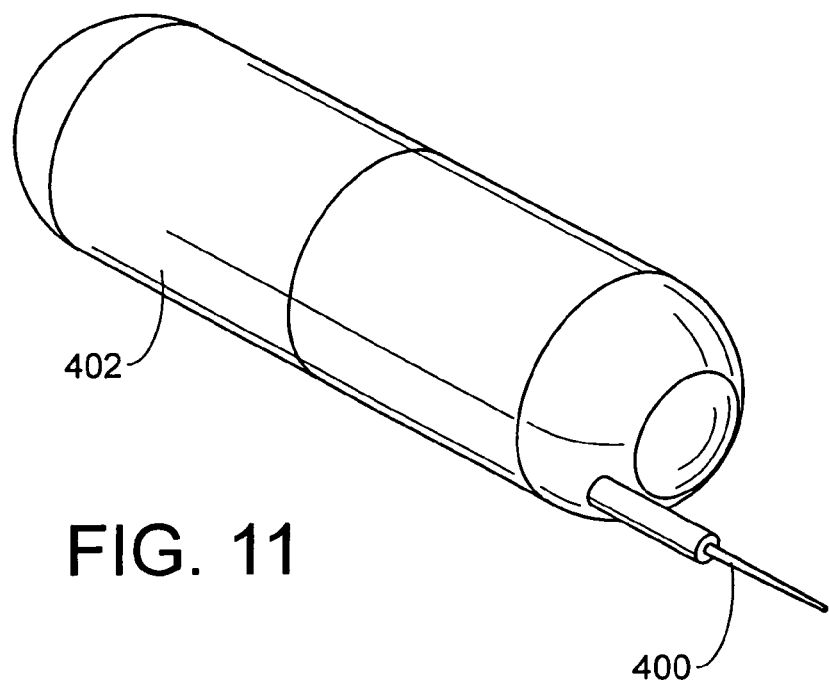
FIG. 11 is a perspective view of a capsule with a treatment tool such as a retractable needle or retractable catheter for injection or retrieval in accordance with a ninth embodiment of the present invention.

In a ninth embodiment (FIG. 11), a treatment tool 400 for injection or retrieval (such as a needle or catheter) would be added to capsule 402. The tool 400 would be retractable into the capsule. A needle would be a sclerotherapy needle to sclerose a dilated vein. Alternatively, the needle could provide epinephrine to a bleeding vessel to stop bleeding. Also, tool 400 can include a thin wire, catheter, or a miniature plastic or metal stent can be deployed in the biliary and pancreatic ducts in other forms of the capsule.

Figure 12:
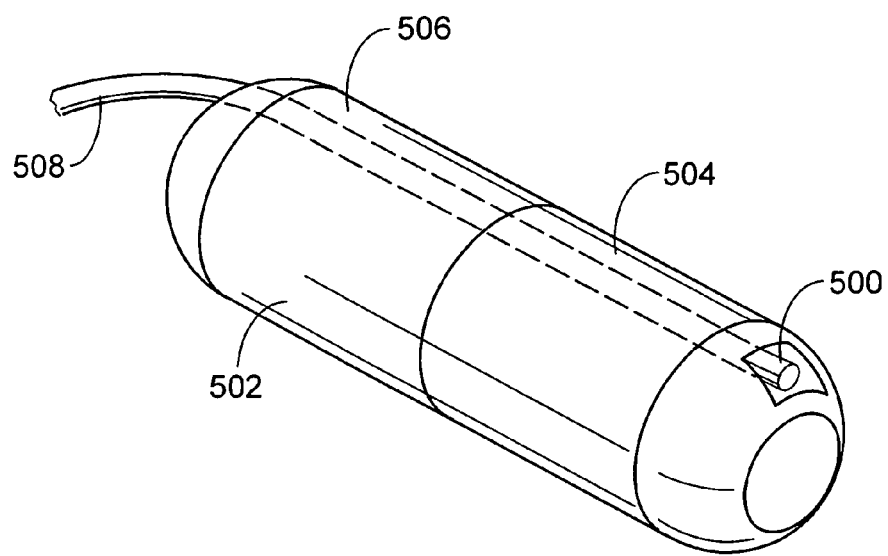
FIG. 12 is a perspective view of a capsule with a suction port and suction tube in accordance with a tenth embodiment of the present invention.

In a tenth embodiment (FIG. 12), a suction port 500 is provided in capsule 502. The suction port 500 would pass through the capsule from anterior portion 504 to posterior portion 506 of the capsule. Fluid is then suctioned through a suction tube 508 through the suction port of the capsule. The capsule would have suction capabilities to remove unwanted debris and can sprinkle water and n-acetyl cysteine locally over the lens or capsule to remove residual debris from the gastrointestinal system to improve or enhance visualization, diagnostic, therapeutic or other functions of the capsule.

Figure 13:
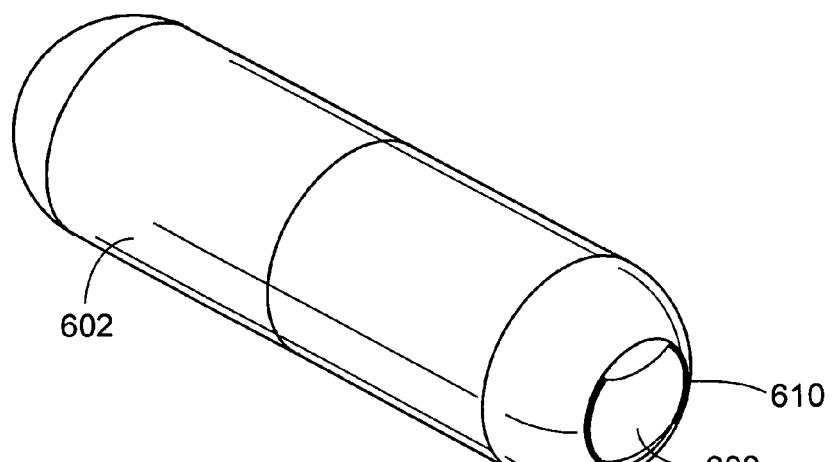
FIG. 13 is a perspective view of a capsule with a rotating lens and wiper in accordance with an eleventh embodiment of the present invention.

In an eleventh embodiment referring to FIG. 13, a rotating lens 600 for capsule 602 is provided which rotates on an axis (not shown). The lens contains a small amount of liquid (such as alcohol with n-acetylcysteine or water) to clean the surface of the lens with a rotating wiper 610. The wiper rotates on the same axis as the lens.

Figure 14A:
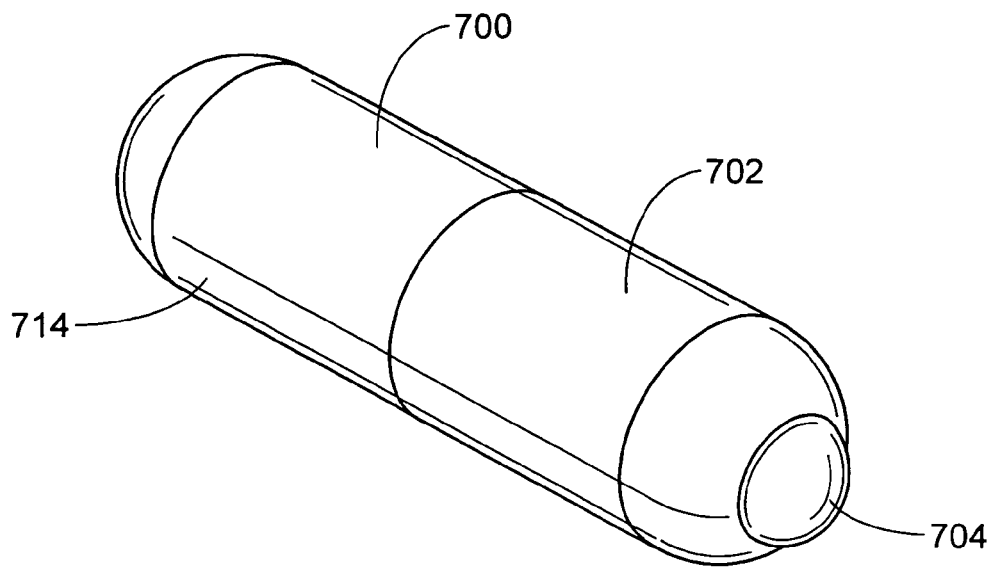
FIG. 14A is a perspective view of a capsule with an ultrasound sensor port in accordance with a twelfth embodiment of the present invention.
Figure 14B:
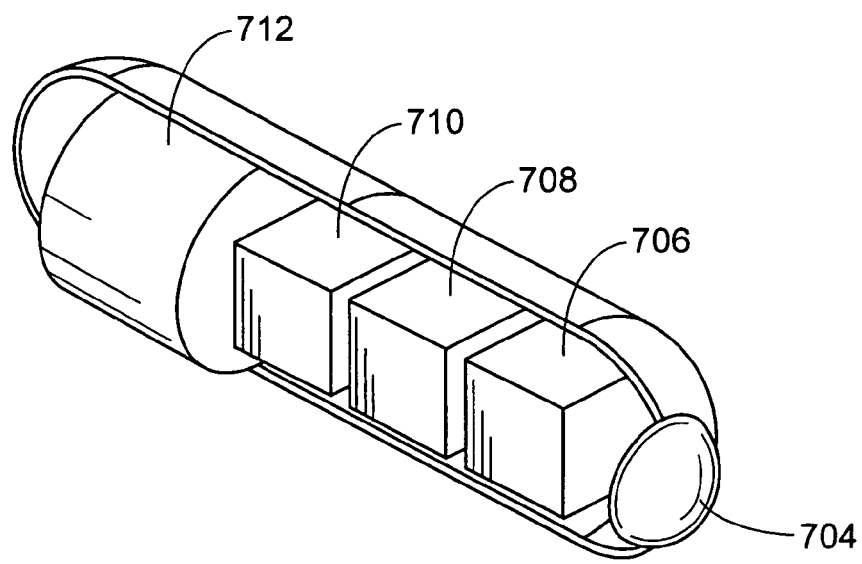
FIG. 14B is an exploded, perspective view of the capsule of FIG. 14A.

Referring to FIGS. 14A and 14B, in a twelfth embodiment, a capsule 700 would comprise an anterior membrane 702 with a port 704 for an ultrasound sensor 706, a transmitter 708, a pose beacon 710, a power source 712, and a posterior membrane 714. The capsule would not include an imaging device or lens.

The anterior membrane 702 is made of a non-allergenic, nondigestible, impervious material. The port 704 is curved to match the curvature of an outside surface of the anterior membrane. The posterior membrane 714 is also made of a non-allergenic nondigestible impervious material, and may include an integrated antenna (not shown) for the transmitter. Embodiments illustrated in FIGS. 6-13 and discussed above can also be incorporated into capsule 700.

Each of the treatment tools 202, 300 and 400 can be connected to an elevator device (not shown) which is used to elevate or lift the treated tools through different angles with a remote control device adding an additional 180° of range of movement.

Each capsule can include a reception capability, such as a radio-frequency receiver, and an internal microprocessor that allows instructions to be relayed from the physician to the capsule. Miniature motors allow the imaging system to be reoriented, or provide some form of "controlled mobility," which could include a remote control, joystick, mouse control or other computer-directed or voice-directed control or other control (not shown). An expandable bladder attached to the capsule can be expanded to stabilize the capsule or slow its motion through the tract. The system may also include on-board signal processing circuitry to automatically stabilize the image. Alternatively, a micro-machined mechanical stabilization platform can be built into the imaging system. The imaging system may also include a means such as a prism or fiber-optic device, to direct multiple images onto the imaging device.

The invention has been described with reference to a preferred initial embodiment. Obviously, alterations and modifications will occur to others upon a reading and understanding of this specification. It is intended to include all such modifications and alternations insofar as they come within the scope of the appended claims or the equivalents thereof.

Having thus described the preferred embodiment, the invention is now claimed:

1. An imaging device comprising:
   a membrane defining an internal cavity and being provided with a window; wherein said window has a flat surface;
   a lens disposed in relation to said window;
   a light source disposed in relation to said lens for providing illumination to outside of said membrane through said window;
   an imaging array disposed in relation to said lens, wherein images from said lens impinge on said imaging array;
   a treatment tool which provides at least one of a functional and therapeutic function, the treatment tool being accessible to the exterior of said imaging device via a port comprising an opening in the membrane;
   an elevation device connected to said treatment tool for raising or lifting said treatment tool through a plurality of angles; and
   a transmitter disposed in relation to said imaging array for transmitting a signal from said imaging array to an associated transmitter outside of said capsule, said lens, light source and projection device, imaging array, and transmitter being enclosed within said internal cavity.

2. The imaging device of claim 1 further comprising at least one pair of wheels extending from said membrane.

3. The imaging device of claim 1 further comprising at least one pair of fins extending from said membrane.

4. The imaging device of claim 1 further comprising at least one pair of prongs extending from said membrane for stabilizing said device.

5. The imaging device of claim 1 wherein said treatment tool includes a miniature laser device positioned within said opening.

6. The imaging device of claim 1 wherein said lens is rotatable about an axis.

7. The imaging device of claim 6 further comprising a rotatable wiper mounted on said lens which cleans an exterior surface of said lens.

8. An imaging device comprising:
   an anterior membrane;
   a posterior membrane connected to said anterior membrane, said anterior membrane and said posterior membrane define an internal cavity;
   a lens disposed on an outside surface of said anterior membrane;
   a light source and projection device disposed in relation to said lens for providing illumination to outside of said anterior membrane;
   an imaging array disposed in relation to said lens, wherein images from said lens impinge on said imaging array;
   a transmitter disposed in relation to said imaging array for transmitting a signal from said imaging array to an associated transmitter outside of said capsule;
   a pose beacon positioned in relation to said transmitter;
   said light source and projection device, imaging array, transmitter, and pose beacon are enclosed within said internal cavity; and
   at least one pair of wheels extending from at least one of said anterior membrane and said posterior membrane to provide a therapeutic and a locomotive function.

9. The imaging device of claim 8, further comprising a power source which provides power to said imaging array, said transmitter and said light source and projection device.

10. The imaging device of claim 8, wherein said anterior membrane is made of a non-allergenic, non-digestible, impervious material.

11. The imaging device of claim 8, wherein said posterior membrane is made of a non-allergenic, non-digestible, impervious material.

12. The imaging device of claim 8 further comprising at least one pair of fins extending from one of said anterior membrane and said posterior membrane.

13. The imaging device of claim 8 further comprising at least one pair of prongs extending from said posterior membrane for stabilizing said device.

14. The imaging device of claim 8 further comprising a port comprising an opening for a miniature laser device and a miniature laser device positioned within said opening.

15. The imaging device of claim 14 further comprising an elevation device connected to said miniature laser device for raising and lowering said miniature laser device, said elevation device being controlled by an external source.

16. The imaging device of claim 8 wherein said lens is rotatable about an axis.

17. The imaging device of claim 16 further comprising a rotatable wiper mounted on said lens which cleans an exterior surface of said lens.

18. An imaging system comprising:
    a capsule, said capsule comprising:
       an anterior membrane, said membrane comprises a window; wherein said window has a flat surface;
       a posterior membrane connected to said anterior membrane, said anterior membrane and said posterior membrane define an internal cavity;
       at least one pair of fins extending from at least one of said anterior membrane and said posterior membrane to aid locomotion in a fluid-filled environment;
       a lens disposed in relation to said window;

a light source and projection device disposed in relation to said lens for providing illumination to outside of said anterior membrane;

an imaging array disposed in relation to said lens, wherein images from said lens impinge on said imaging array;

a first transmitter disposed in relation to said imaging array;

a pose beacon positioned in relation to said transmitter;

said lens, light source and projection device, imaging array, transmitter, and pose beacon are enclosed within said internal cavity;

a second transmitter located outside of said capsule, said first transmitter transmits a signal from said imaging array to said second transmitter;

a pose detection system outside of said capsule, said pose detection system tracks said pose beacon; and a recording and display device, said pose detection system relays tracking information to said recording and display device.

19. The imaging system of claim 18 further comprising at least one pair of wheels extending from one of said anterior membrane and said posterior membrane.

20. The imaging system of claim 18 further comprising at least one pair of prongs extending from said posterior membrane for stabilizing said capsule.

21. The imaging system of claim 18 further comprising a port comprising an opening for a miniature laser device and a miniature laser device.

22. The imaging device of claim 21 further comprising an elevation device connected to said miniature laser device for raising and lowering said miniature laser device, said elevation device being controlled by an external source.

23. The imaging system of claim 18 wherein said lens is rotatable about an axis.

24. The imaging system of claim 23 further comprising a rotatable wiper mounted on said lens which cleans an exterior surface of said lens.

* * * * *